(12) United States Patent
Weigl

(10) Patent No.: US 10,254,238 B2
(45) Date of Patent: Apr. 9, 2019

(54) METHOD FOR AT LEAST QUALITATIVELY DETERMINING AT LEAST ONE PHYSICAL AND/OR CHEMICAL PROPERTY OF A LAMINATE PANEL

(71) Applicant: FLOORING TECHNOLOGIES LTD., Pieta (MT)

(72) Inventor: Martin Weigl, Vienna (AT)

(73) Assignee: FLOORING TECHNOLOGIES LTD., Kalkara (MT)

( * ) Notice: Subject to any disclaimer, the term of this patent is extended or adjusted under 35 U.S.C. 154(b) by 19 days.

(21) Appl. No.: 14/891,878

(22) PCT Filed: Jun. 17, 2014

(86) PCT No.: PCT/EP2014/001640
§ 371 (c)(1),
(2) Date: Nov. 17, 2015

(87) PCT Pub. No.: WO2014/202205
PCT Pub. Date: Dec. 24, 2014

(65) Prior Publication Data
US 2016/0131606 A1    May 12, 2016

(30) Foreign Application Priority Data

Jun. 18, 2013 (EP) ...................... 13003104

(51) Int. Cl.
*G01N 25/18* (2006.01)
*G01N 29/04* (2006.01)

(52) U.S. Cl.
CPC ............. *G01N 25/18* (2013.01); *G01N 29/04* (2013.01); *G01N 29/045* (2013.01); *G01N 2291/0231* (2013.01); *G01N 2291/2632* (2013.01)

(58) Field of Classification Search
CPC ....... G01N 29/045; G01N 25/18; G01N 29/04
(Continued)

(56) References Cited

U.S. PATENT DOCUMENTS 5,698,787 A     12/1997  Parzuchowski et al.
6,813,927 B1 *  11/2004  Harris ................. G01N 3/48
                                                            73/12.09
(Continued)

FOREIGN PATENT DOCUMENTS

DE         0152422          11/1981
DE       152422 A   *       11/1981
(Continued)

OTHER PUBLICATIONS

Mobile Devices Teardown: What's inside Samsung's Galaxy S4? George Leopold Nov. 30, 2012 http://electronics360.globalspec.com/article/94/teardown-what-s-inside-samsung-s-galaxy-s4 May 4, 2017.*

(Continued)

*Primary Examiner* — Natalie Huls
*Assistant Examiner* — Monica S Young
(74) *Attorney, Agent, or Firm* — Andrew M. Calderon; Roberts Mlotkowski Safran Cole & Calderon, P.C.

(57) ABSTRACT

The invention relates to a method for at least qualitatively determining at least one physical and/or chemical characteristic of a laminate panel (2) by means of a mobile radio device (14), wherein the method comprises the following steps: (a) arranging the mobile radio device (14) on a surface (10) of the laminate panel (2); (b) measuring at least one physical and/or chemical measurement variable by means of a measurement instrument (28) integrated into the mobile radio device (14); and (c) at least qualitatively determining (Continued)

the at least one physical and/or chemical characteristic from the at least one measured physical and/or chemical measurement variable.

17 Claims, 2 Drawing Sheets

(58) Field of Classification Search
USPC .......................................................... 374/44
See application file for complete search history.

(56) References Cited

U.S. PATENT DOCUMENTS

| | | | | |
|---|---|---|---|---|
| 7,066,007 | B2* | 6/2006 | Ziegler | G01N 9/36 |
| | | | | 73/12.12 |
| 7,603,904 | B2* | 10/2009 | Harris | G01B 17/00 |
| | | | | 702/56 |
| 2008/0295602 | A1* | 12/2008 | Wallace | G01N 3/30 |
| | | | | 73/602 |
| 2011/0135872 | A1 | 6/2011 | May et al. | |
| 2011/0302050 | A1* | 12/2011 | Kildevaeld | G06Q 30/06 |
| | | | | 705/26.7 |
| 2013/0023738 | A1 | 1/2013 | Chang et al. | |
| 2013/0102359 | A1 | 4/2013 | Ho | |

FOREIGN PATENT DOCUMENTS

| | | |
|---|---|---|
| RU | 2011137769 | 3/2013 |
| WO | 2007058926 | 5/2007 |

OTHER PUBLICATIONS

Feb. 2012 http://www.dummies.com/consumer-electronics/tablets/samsung-galaxy-tab/how-to-set-sound-options-on-your-samsung-galaxy-tab/; "Gookin".*
Tech Aug. 22, 2011 07:13 pm ET Updated Oct. 22, 2011 Melon Meter App Uses IPhone Microphone to Rate Your Watermelon Jason Gilbert.*
English Translation of DD 152422 A.*
Jason Dorrier, "Sensors in Smartphones: Galaxy S4 Adds Pressure, Temperature, and Humidity Sensors", Retrieved from the Internet on Apr. 1, 2013, 3 pages.
Smart Tools Co., "Smart Tools Co—Google Play Store", Google, Retrieved from the Internet on Aug. 8, 2013, 3 pages.

* cited by examiner

METHOD FOR AT LEAST QUALITATIVELY DETERMINING AT LEAST ONE PHYSICAL AND/OR CHEMICAL PROPERTY OF A LAMINATE PANEL

The invention relates to a method for at least qualitatively determining at least one physical and/or chemical property of a laminate panel by means of a mobile wireless device and a corresponding mobile wireless device.

The physical and/or chemical properties of a laminate panel are at least partially decisive for a purchase decision of a customer in many fields. These physical properties can be, for example, a thermal insulation or sound damping property. The shielding of electromagnetic fields can also be such a physical property which is decisive for purchase.

The chemical properties which can influence the purchase decision of a customer include in particular the outgassing properties of a laminate panel. Depending on the materials used during the production of the laminate panel, it is possible that specific substances, for example, formaldehyde, can outgas from the laminate panels. Since these substances can be harmful to health, the question of how many of these substances are emitted from the laminate panels is of great interest for the customer. Of course, other substances can also escape from the laminate panel. These comprise in particular organic substances, for example, volatile organic compounds (VOC), but also other substances which can possibly be more or less harmful to health.

Laminate floor panels, for example, presently have to fulfill a variety of different requirements and have a variety of different properties. For example, if a room is designed having a laminate floor, a room sound or walking sound occurs when walking on this floor, which is perceived in the room designed having the laminate floor. In addition, footstep sound arises, which can be perceived in a room located below this room. Both the room sound or walking sound and also the footstep sound are to be as low as possible in this case, to induce the least possible annoyance of the occupants by the noises.

Laminate floors and laminate panels are material composites, which preferably have an internal carrier plate and coatings on the large-area upper and lower sides. Plate-shaped wooden materials, for example, high-density fiberboards (HDF) are typically used as carrier plates for this purpose. The surfaces of these HDF slabs are finished by different methods to achieve the desired product properties, for example, the abrasion resistance, the scratch resistance, the resistance in relation to external shock-type force action or the like. Depending on the usage class according to EN 13329, requirements of different levels are placed on the product surface and the overall material, in particular for the mentioned properties.

Laminate panels and laminate floors have a decorative layer, which is applied either directly to the material, for example, by direct printing, or beforehand on a decorative paper to be applied. Such a decorative paper can in turn either be impregnated by a resin or be non-impregnated at the point in time of the application. In the case of direct printing, in which the decoration is printed directly onto the carrier plate, this can be performed after corresponding surface pretreatment of the carrier plate by indirect gravure printing or by means of digital printing.

The sealing of the surface can also be performed by different methods. Lacquer systems, which cure, for example, by means of UV radiation or electron radiation or autocatalytically, or resins can be used. In this case, different lacquer systems are usable depending on the requirement and the technology used.

Melamine resins are typically used for sealing the surface by means of resins, which are applied, for example, as an overlay paper, liquid overlay, or powdered overlay onto the surface to be sealed. The curing is typically performed in short cycle presses under the action of temperature and pressure.

The lower side of the carrier plate can be sealed in simplified methods, but in principle using the same technologies as the decorative upper side. In addition, a counter layer can be applied to the lower side, to thus reduce the internal tensions in the laminate panel or the floor laminate, which originate from the coating of the upper side.

The finishing of the sides of the carrier plate is conventionally performed on half-format plates, which have, for example, an edge length of 2800×2070 mm. Depending on the facility used, a so-called multiple length can also be used, which can have, for example, two or three times the length of such a half-format plate.

In the course of the further processing, the plates are then severed to form individual panels, on which, for the lateral connection of individual panels to form a laying composite, connecting means are attached, for example, like a tongue and groove having locking elements, which are either worked out integrally from the carrier material or are provided as separate components.

The laminate panels thus produced are packaged in small piece counts into packets, so that often a part of the decorative surface of the laminate panels is visible.

Melamine-resin-coated laminate floors generally have two pronounced properties. On the one hand, a substantial volume shrinkage occurs during the curing as a result of a condensation process. This results in substantial tensions in the melamine resin layer, so that in the event of mechanical excitations, the above-described noises and acoustically perceptible oscillations arise. In addition, melamine resins have increased thermal conductivity in comparison to other artificial resins, for example, so that the floor is perceived to be cold when it is walked on barefoot, for example, since the body heat is dissipated strongly by way of the melamine resin. Other artificial resins or lacquers and lacquer systems used in the production of laminate panels have a lower thermal conductivity in comparison to melamine resin, so that a floor which consists of laminate panels produced using these materials is not perceived as this cold.

However, it is disadvantageous that the customer, for example, in a specialized store for such objects, for example, laminate floor panels, cannot ascertain or test these physical and/or chemical properties him- or herself, and thus cannot compare the properties of different products, possibly from different producers, with one another. He or she is referred to often vague advertising statements, for example, "good noise damping properties", which make a comparison of different products impossible. This is additionally made more difficult in that in particular such properties, as a result of the very high level of subjectivity in the perception, are often properties which are difficult to objectively detect. The specifications of technical properties are often specified based on testing certificates, for example. However, these are often not known or are not comprehensible to laypeople, so that such a specification is often of little help for the final customer.

The invention is therefore based on the object of specifying a method for at least qualitatively determining at least one physical and/or chemical property of a laminate panel, which can be carried out directly on the laminate panel rapidly and without a large expenditure for apparatus.

The invention achieves the stated object by way of a method for at least qualitatively determining at least one physical and/or chemical property of a laminate panel by means of a mobile wireless device, wherein the method has the following steps (see FIG. 2):

a) arranging the mobile wireless device on a surface of the laminate panel (200), b) measuring at least one physical and/or chemical measured variable by means of a measuring instrument integrated in the mobile wireless device (210), and c) at least qualitatively determining the at least one physical and/or chemical property from the measured at least one physical and/or chemical measured variable (220).

Present mobile wireless devices, in particular smart phones, have a variety of different functions, which are enabled by measuring instruments integrated in the mobile wireless device. Measuring instruments can be provided in this case as individual sensors or measured value recorders or as a measurement chain consisting of multiple elements, which has a measuring transducer or a computing device, for example. These measuring instruments are used in the method according to the invention to measure at least one physical and/or chemical measured variable of the laminate panel and to at least qualitatively determine the at least one desired physical and/or chemical property from the measured values thus obtained. For this purpose, it is only necessary to arrange the mobile wireless device on the surface of the laminate panel. The region in which the mobile wireless device is arranged on this surface, and in which the mobile wireless device comes into contact with the surface, thus covers or overlaps it, is referred to hereafter as the contact surface. In this case, the mobile wireless device, in particular the smart phone, is advantageously arranged on the surface of the laminate panel so that it is arranged having the side facing away from a display screen of the mobile wireless device on the laminate panel. This is enabled particularly simply in that the mobile wireless device, in particular the smart phone, is laid having the side facing away from the display screen on the surface of the laminate panel.

The measurement of the physical and/or chemical measured variable is carried out via a program which is stored, for example, in the data memory of the mobile telephone, a so-called "app".

It has proven to be particularly advantageous if the physical and/or chemical measured variable is measured multiple times at different points in time. Thus, for example, the time curve of the measured variable can be ascertained and the physical and/or chemical property can be at least qualitatively determined therefrom. In this manner, transportation variables, for example, thermal conduction and sound conduction properties, for example, can also be determined from the time curve of the temperature or the noise.

Method steps a) and b) are preferably carried out for different laminate panels and the qualitative determination of the physical and/or chemical properties takes place by way of comparison of the measured variables measured in the different laminate panels. This is advantageous in particular for the case in which, for example, an exact numeric value is not required for the physical and/or chemical property, but rather the physical and/or chemical property of multiple laminate panels, which can be floor laminate panels of different producers, for example, are merely to be compared. Therefore, it can be ascertained easily and rapidly by the customer him- or herself at the purchase point by way of this method which of the laminate panels has, for example, the best thermal insulation, footstep sound damping, or shielding of electromagnetic fields or the lowest emission values of various substances, for example, formaldehyde or volatile organic compounds (VOC). The exact numeric value is often not of interest in this case, but rather only, for example, the ratio of these measured values to one another, so that the comparison of the different laminate panels is sufficient for the customer to make a purchase decision.

Of course, it is also possible to carry out the qualitative determination of the physical and/or chemical property by way of a comparison to values stored in the data memory of the mobile wireless device, for example. Thus, for example, it is conceivable that the measured values or the associated physical and/or chemical properties of already existing laminate panels, which are available on the market, for example, floor laminate panels of a producer, are stored in the data memory of the mobile wireless device, in particular the smart phone. These data are preferably provided by an app. If a physical and/or chemical measured variable is now measured, the physical and/or chemical property which is of interest in the respective case can be qualitatively determined therefrom, for example, by way of comparison to the stored values. Thus, even for the case in which only one laminate panel is provided for the user of the method, it can be qualitatively determined whether this laminate panel has, for example, better sound damping properties than other laminate panels which are available on the market, but are currently not present in the store, for example. In this manner, the quality of a laminate panel can be determined in relation to the quality of other laminate panels, without these other panels having to be present.

Preferably, the physical measured variable is the temperature of the laminate panel on the contact surface and the measuring instrument integrated in the mobile wireless device is a thermometer. In particular smart phones, but also other mobile wireless devices, have an integrated thermometer, to be able to provide the current temperature in a retrievable manner to the user. This thermometer can be used, for example, to also determine the temperature of the laminate panel on the contact surface.

This temperature can also be determined in a contactless manner, for example, if the smart phone has, for example, an integrated pyrometer for contactless temperature measurement. To be able to achieve the most reliable and reproducible possible measurement of the temperature, it is to be ensured that air movements, which can arise due to drafts, for example, are avoided, since these can have an influence on the temperature measurements. This is also true for the ambient temperature, which can in particular advantageously be determined and measured beforehand using the thermometer of the mobile wireless device. In this manner, further environmental factors, which can have an influence on the measurement, can be eliminated or determined and incorporated into the measurement or the later analysis of the measured values.

A thermal conductivity and/or a thermal insulation capability of the laminate panel is advantageously determined from the temperature measured at various points in time. For this purpose, the temperature of the laminate panel can preferably be increased before the measurement of the temperature. This can preferably be performed on the contact surface. However, a temperature increase at a predetermined distance to the contact surface can also be used. After the temperature has been increased at this point, the temperature can be determined at various successive points in time by means of the thermometer integrated in the mobile wireless device, so that the cooling of the laminate panel on the contact surface can be tracked and documented. Material properties, for example, the thermal conductivity and/or the thermal insulation capability of the laminate panel, can be determined from this decay behavior.

The temperature on the contact surface of the surface of the object is advantageously increased by a temperature increase in the mobile wireless device. This can be achieved, for example, in that an electrical resistor which is integrated in the mobile wireless device is used to generate heat, in that, for example, a current is conducted through it. Of course, other possibilities are also conceivable for introducing heat into the surface of the laminate panel, in that a function of the mobile wireless device is used. Thus, for example, a program can be executed in the mobile wireless device, which results in heating of the data processing unit, for example, by which the surface of the laminate panel is also heated on the contact surface. Due to the elevated temperature inside the mobile wireless device, heat is introduced into the contact surface of the surface, so that it heats up.

After the heating of the surface is completed, the temperature is measured at different points in time and the cooling of the contact surface of the laminate panel is thus documented.

Of course, the reverse path is also possible. Instead of firstly heating the contact surface of the surface of the laminate panel and subsequently documenting the cooling procedure by way of multiple measurements of the temperature, the temperature can also be measured at different points in time during the heating of the contact surface of the surface of the laminate panel. However, to determine the thermal insulation capability and/or the thermal conductivity and/or the heat capacity of the respective laminate panel not only qualitatively, but rather also quantitatively in this manner, it is necessary to know the quantity of heat developed in the respective manner and introduced into the surface. The desired variables can subsequently be ascertained from this quantity of heat which is developed and introduced into the surface and from the temperature curve during the heating procedure.

However, for example, a comparison of different laminate panels may also be produced using this method also for the case in which the quantity of heat is not known. For this purpose, the method is successively carried out on different laminate panels, wherein the heating procedure by the claimed function of the mobile wireless device runs identically for all laminate panels. Even if the actual numeric values of the quantities of heat thus introduced into the surface are not known, it can still be presumed that the same quantity is introduced in each case into the surface of the individual laminate panels, so that the heat capacities and/or the thermal insulation capabilities or thermal conductivities of the individual laminate panels which can be ascertained therefrom can be easily compared to one another.

Independently of the manner in which the temperature of the respective laminate panel is determined, it is preferably to be ensured that the external parameters, for example, ambient temperature and, for example, air movements are identical or at least very similar for the measurement at each laminate panel, to be able to ensure a comparability of the results.

Of course, it is also possible not to induce the temperature increase on the contact surface of the surface of the laminate panel by way of a temperature increase in the mobile wireless device. Alternatively thereto, it has proven to be advantageous if the temperature is increased by laying a hand on the contact surface or at a predetermined distance thereto for a predetermined time span, before the mobile wireless device is arranged on the contact surface. However, it is advantageous in this case if both the predetermined time span and also the time span which passes until the mobile wireless device is arranged on the contact surface of the surface are maintained as exactly as possible, to achieve reproducibility of the results. This is necessary in particular if this method is to be carried out for different laminate panels and the subsequently obtained results are to be compared. To be able to maintain and measure this predetermined time span as precisely as possible, for example, the mobile wireless device can display the time which has already passed or still remains via the display screen, for example. This can be performed in the form of a countdown, for example.

In a special embodiment of this method, via the thermometer of the mobile wireless device, only the starting temperature before the hand is laid on the contact surface of the laminate panel and the final temperature after the laying of the hand are determined. In this manner, the temperature difference can be calculated and the physical property can thus be determined.

In addition to the physical properties determined by the temperature, such as thermal conductivity and thermal insulation capability, the sound properties are of great significance for the purchase decision of a customer, in particular in the case of floor laminate panels.

The physical measured variable is advantageously the sound of an acoustic signal, which is measured by means of a microphone integrated in the mobile wireless device, wherein the acoustic signal is generated in the laminate panel before the measurement of the sound. This is advantageous in particular for floor coverings, for example, floor laminate panels, to determine the sound damping or sound conduction properties of the respective floor covering and thus to determine the noise level due to footstep sound or room sound.

In one advantageous embodiment, the acoustic signal is generated by a vibration function of the mobile wireless device. Mobile wireless devices and in particular smart phones conventionally have such a vibration function, for example, to make the respective user of the mobile wireless device aware of an incoming call, for example, even without an acoustic signal. After the mobile wireless device is arranged on the contact surface, this vibration of the mobile wireless device in the case of activated vibration function is transmitted to the laminate panel and an acoustic signal is thus generated in the laminate panel or excited or induced in the laminate panel.

Alternatively or additionally thereto, the acoustic signal can also be generated by knocking on an upper side and/or lower side of the laminate panel at a predetermined distance to the contact surface. In this case, firstly the mobile wireless device is arranged on the contact surface and subsequently, for example, by knocking using a finger or an object on the surface, the acoustic signal is generated in the laminate panel. It is advantageous in this case if the knocking is generated at a predetermined distance, which is maintained as precisely as possible, to the contact surface of the laminate panel, to obtain a reproducible result. The sound or the acoustic signal in the laminate panel is measured via the microphone integrated in the mobile wireless device. Properties, for example, the sound damping property, can be determined via the volume of the acoustic signal thus measured. If the distance at which the acoustic signal was generated from the contact surface is simultaneously also known, statements can also be made, for example, about the sound conduction property and sound conductivity of the laminate panel.

An acoustic signal consists in this case of sound waves, which may be described by frequency and amplitude, i.e., pitch and volume. In particular the volume and the time curve of the volume of an acoustic signal are of interest for the determination of the sound conduction properties and sound damping properties of a laminate panel. Therefore, in the method described here, in particular via the microphone integrated in the mobile wireless device, in particular the volume of the acoustic signal is measured and the measurement signal thus ascertained is further processed. For special applications, it can be advantageous to carry this out in a frequency-dependent manner, for example. This means that, for example, a frequency-dependent sound damping property is determined, in that either the excited or induced acoustic signal only contains sound waves of a specific frequency or a specific frequency band or that, using the microphone provided in the mobile wireless device, only, sound waves of specific frequencies are measured, while the sound waves having other frequencies are filtered out. This is controllable, for example, by specific software. Of course, combinations of these two possibilities are also conceivable.

The method can also be successively carried out for different laminate panels during the determination of the sound properties, so that the thus ascertained results can be set in relation to one another and can be compared to one another. Also in this case, the exact numeric value, for example, of the sound conductivity or sound damping capability is often not of interest, but rather the purchase decision is often made in dependence only on a comparison of these properties for different laminate panels.

The generation of the acoustic signal by knocking on the upper side and/or lower side of the laminate panel is advantageously carried out at a distance of less than 10 cm, advantageously less than 8 cm, in particular less than 5 cm. In this case, the volume of the sound or of the acoustic signal can also be measured at different successive points in time, so that, for example, the reverberation of the generated signal can also be measured and acquired. As already in the case of the measurement of the temperature, reference values of existing products and laminate panels can also be provided for the measurement of the sound or of the acoustic signal, for example, by an app, and stored in the electronic data memory of the mobile wireless device and used for the comparison of the measured variable which is measured or the specific physical properties.

In this manner, a sound conductivity and/or a sound damping capability of the laminate panel can advantageously be determined from the sound or other measured variables of an acoustic signal which are measured at various points in time.

In addition to the physical and/or chemical properties which are dependent on temperature and sound, it can be advantageous for specific applications if the laminate panel is capable, for example, of shielding magnetic fields.

The physical measured variable is preferably a magnetic field strength, which is measured by means of a magnetometer integrated in the mobile wireless device. The compass, which is often integrated in mobile wireless devices and in particular smart phones, contains a magnetometer. It measures properties of the magnetic field of the earth, for example, the alignment thereof, and thus determines the respective compass direction. The magnetometer contained for this purpose in the mobile wireless device for measuring the magnetic field strength and the magnetic field direction is used in the present method to measure the magnetic field strength as a physical measured variable. For example, to determine the shielding capability for magnetic fields of a laminate panel, the magnetic field strength is measured once as a physical measured variable when the mobile wireless device is arranged on the contact surface of the laminate panel. A second measurement is carried out when the mobile wireless device is not arranged on the contact surface. The difference of the two magnetic field strengths is a measure of the shielding capabilities of the respective object. The actual numeric value of the magnetic field strength is also often not of interest in this case. Rather, in the case of the shielding capability of magnetic fields, the comparison of multiple laminate panels to one another is also more important, so that the method is also carried out in this case using a plurality of different laminate panels, wherein the shielding capabilities ascertained in each case can be compared to one another. For this purpose, a comparison measurement without a laminate panel is not necessary.

While the direction of the Earth's magnetic field is determined for the compass function of the smart phone, to thus ascertain the magnetic north pole, in particular the strength of the magnetic field has to be determined and set in relation to one another for different measurements to carry out the method described here. For this purpose, the laminate panels to be compared are to be measured at the same location, to thus achieve a comparability of the results. For example, if laminate panels in different department stores or do-it-yourself stores are compared to one another, changed measurement results can occur due to the different structural embodiment of the respective building. For example, if a basement having a reinforced concrete ceiling, for example, is arranged below the do-it-yourself store, the Earth's magnetic field can already be shielded by this arrangement, while this is not the case or is the case to a different extent in buildings without a basement, for example. A comparability of the measurements is possible only with difficulty or not at all without precise knowledge of these circumstances. A comparability of the measurement results thus obtained is only provided for the case in which the individual laminate panels are measured at the same location.

In particular for laminate panels which are to be used in living spaces, for example, as a floor or wall covering, it is of great interest for the final customers to know the chemical properties of such laminate panels.

Advantageously, a quantity of a substance outgassing from the laminate panel is measured in this case during the measurement of the at least one physical and/or chemical measured variable. This can be, for example, formaldehyde or a volatile organic compound (VOC). Of course, other substances, which can possibly outgas from laminate panels, are also conceivable.

In particular for substances which are harmful to health, it is advantageous if the respective laminate panel emits the least possible quantity of this substance. Since the producers of corresponding laminate panels therefore ensure that the outgassing quantity is as small as possible, it can be advantageous, to increase the measurement accuracy of the method described here, to increase the temperature at least on the contact surface of the upper side of the laminate panel, for example, and therefore to also temporarily increase the outgassing quantity of the respective substance. The quantity to be measured of the emitted substance is thus sufficiently large that a reliable and accurate measurement is possible. If the temperature on the contact surface of the upper side of the laminate panel is measured at the same time, different laminate panels, optionally from different producers, may also be compared with one another well in this case.

The physical and/or chemical properties described here, which can be determined using a method according to the invention, are only exemplary embodiments of the method described here. In particular, further chemical and/or physical properties can be determined.

In addition, it is possible to determine a plurality of the mentioned properties simultaneously, since the respective measuring instruments used, which are present in the mobile wireless device, often operate independently of one another and in addition the respective physical and/or chemical measured variables do not influence one another or even influence one another in an advantageous manner. As already described, it can be advantageous for the determination of the quantity of an outgassing substance to also determine the temperature of the laminate panel, in particular on the contact surface. Simultaneously, for example, the magnetic field strength could also be determined via the magnetometer. The various physical and/or chemical measured variables do not influence one another. A sound measurement or the determination of the volume of an acoustic signal, in contrast, is possibly not combinable with all other measurements, without influencing the determined measured values in the case of other properties, because of interfering vibrations which have to be generated or induced in the laminate panel.

Advantageously, the mobile wireless device is a smart phone and/or the laminate panel is a floor panel.

Although the methods described here were described in the present case for floor panels, they are also conceivable and executable for other panels. Using the methods described here, different physical and/or chemical properties of laminate panels may therefore be determined rapidly and easily by means of a smart phone, so that a very low expenditure for apparatus and almost no additional costs for the respective user occur.

Of course, the methods according to the invention are not restricted to the described embodiments. Many mobile wireless devices, in particular smart phones, have further measuring instruments, using which greatly varying measured variables can be recorded and thus various physical properties of laminate panels can be determined. Current mobile wireless devices have a camera, for example. Using this camera, it is possible, for example, to photograph and record a decoration of a laminate panel, so that this decoration can be easily compared to other decorations, for example, which have been recorded from other laminate panels. A decoration recognition, in which it is determined, for example, which wood is to be imitated by the decoration, is also possible. For this purpose, data sets of the grain and/or colors and color distributions of the different types of wood, which can be compared to the photographed decoration, are to be stored in the data memory of the mobile telephone.

Via such a photographed decoration, for example, the printing quality, for example, the resolution of the applied print, can also be checked, determined, and thus compared to the determined print quality of other laminate panels. A color determination and a color comparison of different decorations which were thus recorded is also possible. Laminate panels are often used for floors, which are to be replaced, for example, during a renovation of a room or a house. In this case, already present items of furniture are often used further, so that it is advantageous and desirable for aesthetic reasons if the already present items of furniture match with respect to color with the selected decoration of the laminate panels. The selection of the same types of wood or the imitation of the same types of wood for furniture and laminate panels is often not sufficient in this case, since significant differences can also be present here, for example, in the coloration and in the structuring of the decoration. Using the app described here, it is therefore possible to photograph a piece of furniture, for example, a cabinet or a table, for example, and to determine a prevailing color or a color temperature, for example. The same can subsequently be performed with a laminate panel, so that the colors thus recorded can be compared to one another.

In addition, for example, the packets in which the laminate panels are packed or also the laminate panels themselves can be provided with chips, for example, RFID chips. These chips react to emitted electromagnetic radiation, which can be emitted from the mobile wireless device, for example. The RFID chip is thus activated and can transmit items of information, for example, about product details but also availability, delivery times, or product locations in a do-it-yourself store or a large warehouse, to the mobile telephone. Therefore, further items of information about the laminate panels can be ascertained via the smart phone or the mobile telephone.

A computer program according to the invention having program code means is stored in particular on a machine-readable carrier and is configured to carry out a method described here when the computer program runs on a data processing unit of a mobile wireless device. This can be in particular the data processing facility of a smart phone. The computer program is stored in the electronic data memory of the smart phone or another mobile wireless device and can be started, for example, via an operating element, which can be a touchscreen, for example.

The computer program, which can be designed as a so-called "app", can be stored on a central server and provided for download, for example.

A mobile wireless device according to the invention, in particular a smart phone, comprises an integrated thermometer and/or an integrated microphone and/or an integrated magnetometer, for example, for a compass function, and/or further measuring devices and/or a camera and an electrical controller, which is configured to carry out a method according to one of the preceding claims. A corresponding mobile wireless device preferably has an electronic data memory and an electronic data processing facility. A program, a so-called "app", which can be downloaded for free or upon payment of a cost, for example, is advantageously stored in the electronic data memory. This program is executed in the electronic data processing facility of the mobile wireless device, so that the methods described here can be carried out Therefore, product-specific items of information for different laminate panels may be easily collected and stored using a method according to the invention and/or a mobile wireless device according to the invention. These items of information can be used for processing in continuing programs or, for example, stored in a databank. In this manner, for example, products which were evaluated and studied at different sellers can be compared to one another at leisure at a later point in time, so that the purchase decision can be made on a better basis, which is as objective as possible. A presence in the respective sales room of one of the sellers is no longer necessary for this purpose.

After the program has been stored once on the mobile wireless device, no further costs result for the user. The producer of corresponding laminate panels can also provide the "app", i.e., the electronic data processing program, at no cost, for example, so that no additional costs at all arise for the user of the mobile wireless device. The physical and/or chemical properties of the respective laminate panels, which are otherwise difficult to acquire for laypeople, become objectively comparable with one another simply and reliably in this manner. Possibly vague and imprecise advertising statements of different producers no longer have to be used.

In principle, such a method is conceivable for any physical and/or chemical property of a laminate panel, for which there is a corresponding physical and/or chemical measured variable, which is measurable by a measuring instrument integrated in the mobile wireless device. The measured variables listed here of temperature, sound or volume, and magnetic field strength and also the quantity of an outgassing or emitted substance, for example, formaldehyde or VOC, are thus only to be interpreted as examples and not as restrictive. It is also conceivable to provide separate measuring instrument modules for smart phones or other types of mobile wireless devices, which can be connected via corresponding data interfaces to the mobile wireless device, so that the method is also executable for physical and/or chemical properties which are not accessible by a measuring instrument integrated by the producer in the mobile wireless device. Such measuring instruments are also considered to be integrated in the mobile wireless device in the meaning of the present invention. It is only important that the measured values of a physical and/or chemical measured variable, which are recorded by a measuring instrument, can be transmitted to the mobile wireless device and processed further therein.

The respective measurement of the corresponding physical and/or chemical measured variable can be performed in this case with a time delay after the activation of the "app" in the mobile wireless device, to preclude operating effects.

An exemplary embodiment of the present invention is explained in greater detail hereafter with the aid of a drawing. In the FIGURE.

Figure 1:
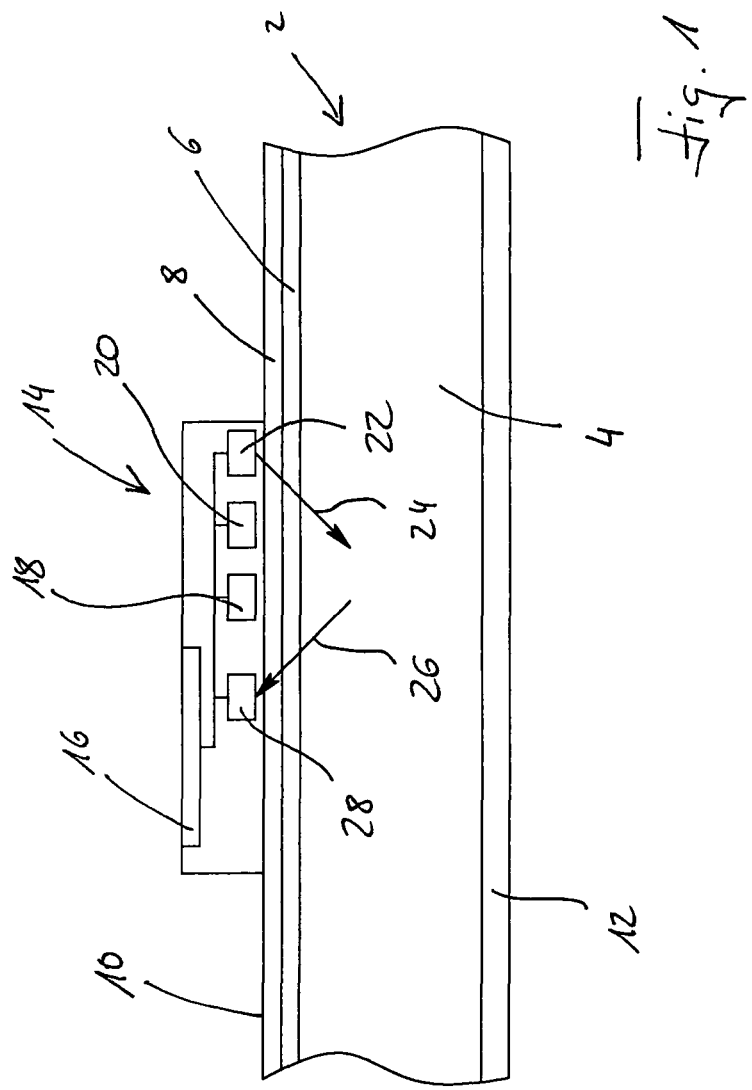
FIG. 1 shows the schematic illustration of a mobile wireless device on a laminate panel.
Figure 2:
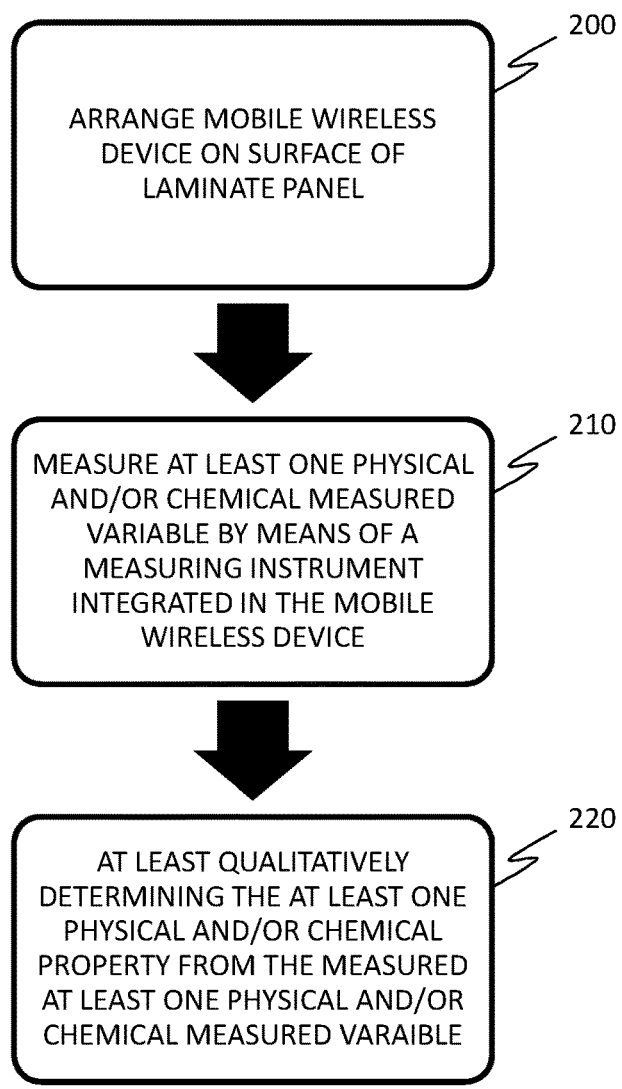
FIG. 2 shows a flowchart of a method for at least qualitatively determining at least one physical and/or chemical property of a laminate panel by means of a mobile device.

FIG. 1 shows a laminate panel 2, which consists of multiple different layers. The laminate panel 2 has a carrier plate 4, on the surface of which, for example, a decorative layer 6 and, above it, an abrasion-resistant layer 8 are arranged. The abrasion-resistant layer 8 forms one surface 10 of the laminate panel. A counter layer 12 is arranged on the side of the carrier plate 4 opposite to the decorative layer 6. This counter layer 12 prevents an upper side and a lower side of the carrier plate 4 from being subjected to different tensile stresses due to the different applied layers. This would result in warping of the laminate panel 2, so-called dishing.

A mobile wireless device 14, which has a display screen 16, is arranged on the surface 10 of the laminate panel 2. The mobile wireless device 14 is arranged with the side facing away from the display screen 16 on the surface 10 of the laminate panel 2. It is sufficient in this case if the mobile wireless device 14 is laid on the surface 10 of the laminate panel 2.

A data processing unit 18 and a data memory 20 are located in the interior of the mobile wireless device, as schematically shown. A program, a so-called app, is stored in the data memory 20, which enables the data processing unit 18 to carry out a method according to the present invention.

In the exemplary embodiment shown in FIG. 1, an emitter 22 is schematically shown, which induces a state change of a physical and/or chemical property, which is indicated by a first arrow 24, in the laminate panel 2. This can be, for example, a sound signal, which is induced by a vibration unit, or a temperature increase, which is induced by, for example, an electrical resistance through which electrical current flows. Other state changes are also conceivable, however. Of course, they do not have to be generated by the mobile wireless device 14.

The laminate panel 2 reacts to this state change, which is indicated by a second arrow 26. This reaction of the laminate panel 2 is detected by a measuring instrument 28. If the state change which is induced by the emitter is, for example, a sound signal, the measuring instrument 28 is a microphone, for example. If the temperature at one point in the laminate panel 2 is changed by the emitter 22, for example, the measuring instrument 28 is advantageously a thermometer. It is important that the state change induced by the emitter 22 can be detected using the measuring instrument 28. Using the values thus ascertained, the method can be executed in the data processing unit 18 and the physical property of the laminate panel 2 can thus be equipped.

LIST OF REFERENCE NUMERALS 2 laminate panel
4 carrier plate
6 decorative layer
8 abrasion-resistant layer
10 surface
12 counter layer
14 mobile wireless device
16 display screen
18 data processing unit
20 data memory
22 emitter
24 first arrow
26 second arrow
28 measuring instrument

The invention claimed is:

1. A method for determining at least one physical or chemical property of a laminate panel by a mobile telephone, wherein the method comprises:
   a) arranging the mobile telephone on a surface of the laminate panel,
   b) measuring at least one physical or chemical measured variable by a measuring instrument integrated in the mobile telephone, and
   c) determining the at least one physical or chemical property from the measured at least one physical or chemical measured variable,
   wherein:
      the steps a) and b) are performed at least once for each of a plurality of different laminate panels and the step c) comprises comparing, among the plurality of different laminate panels, the measured variable,
      the determined at least one physical or chemical property of the laminate panel is displayed by the mobile telephone,
      the at least one physical property comprises any of: thermal conductivity, thermal insulation, heat capacity, thermal conduction, sound conductivity, sound conduction, sound damping, magnetic field strength, magnetic shielding capabilities, print quality or color, and
      the at least chemical property comprises outgassing of a volatile organic compound.

2. The method as claimed in claim 1, wherein the at least one physical or chemical measured variable is measured multiple times at different points in time.

3. The method as claimed in claim 1, wherein the measured physical property is the temperature of the laminate panel on a contact surface, the mobile telephone is in contact with the contact surface, and the measuring instrument integrated in the mobile telephone is a thermometer.

4. The method as claimed in claim 3, wherein a heat source is used to increase a temperature of the laminate panel on the contact surface before the measurement of the at least one physical or chemical measured variable.

5. The method as claimed in claim 4, wherein the heat source used to increase the temperature of the laminate panel on the contact surface is the mobile telephone.

6. The method as claimed in claim 4, wherein the temperature on the contact surface of the laminate panel is increased by laying a hand on the contact surface for a predetermined time span, before the mobile telephone is arranged on the contact surface.

7. The method as claimed claim 1, wherein the measured at least one physical or chemical measured variable comprises the sound of an acoustic signal, which is measured by a microphone integrated in the mobile telephone, wherein the acoustic signal is generated in the laminate panel before the measurement of the sound.

8. The method as claimed in claim 7, wherein the acoustic signal is generated by a vibration function of the mobile telephone.

9. The method as claimed in claim 7, wherein the acoustic signal is generated by knocking on an upper side or lower side of the laminate panel at a predetermined distance to the contact surface.

10. The method as claimed in claim 1, wherein a quantity of a substance outgassing from the laminate panel is measured during the measuring the at least one physical or chemical measured variable.

11. A computer program having program code, stored in a non-transitory computer-readable medium, which is configured to carry out a method as claimed in claim 1 when the computer program runs on a data processing unit of the mobile telephone.

12. A mobile telephone comprising an electrical controller and at least one of an integrated thermometer, an integrated microphone, an integrated compass, or a camera, which is configured to carry out a method as claimed in claim 1.

13. The method as claimed in claim 1, wherein the measuring the at least one physical or chemical measured variable comprises acquiring a photograph of a decoration of the laminate panel.

14. The method as claimed in claim 13, wherein the determining the at least one physical or chemical property from the measured at least one physical or chemical measured variable comprises determining a printing quality of the laminate panel.

15. The method as claimed in claim 14, wherein the printing quality of the laminate panel is determined based on a resolution of the decoration of the laminate panel.

16. A method for determining at least one physical or chemical property of a laminate panel by a mobile telephone, wherein the method comprises:
   a) arranging the mobile telephone on a surface of the laminate panel,
   b) measuring at least one physical or chemical measured variable by a measuring instrument integrated in the mobile telephone, and
   c) determining the at least one physical or chemical property from the measured at least one physical or chemical measured variable,
   wherein:
      the steps a) and b) are performed at least once for each of a plurality of different laminate panels and the step c) comprises comparing, among the plurality of different laminate panels, the measured variable, and the determined at least one physical or chemical property of the laminate panel is displayed by the mobile telephone, and
   the measured physical property is a temperature of the laminate panel on a contact surface, the mobile telephone is in contact with the contact surface, and the measuring instrument integrated in the mobile telephone is a thermometer, and
   a thermal conductivity or thermal insulation capability of the laminate panel is determined from the temperature of the laminate panel measured at various points in time.

17. A method for determining at least one physical or chemical property of a laminate panel by a mobile telephone, wherein the method comprises:
   a) arranging the mobile telephone on a surface of the laminate panel,
   b) measuring at least one physical or chemical measured variable by a measuring instrument integrated in the mobile telephone, and
   c) determining the at least one physical or chemical property from the measured at least one physical or chemical measured variable,
   wherein:
      the steps a) and b) are performed at least once for each of a plurality of different laminate panels and the step c) comprises comparing, among the plurality of different laminate panels, the measured variable, and the determined at least one physical or chemical property of the laminate panel is displayed by the mobile telephone,
   the measured at least one physical or chemical measured variable comprises a sound of an acoustic signal, which is measured by a microphone integrated in the mobile telephone, wherein the acoustic signal is generated in the laminate panel before the measurement of the sound,
   acoustic signal is generated by a vibration function of the mobile telephone, and
   a sound conductivity or sound damping capability of the laminate panel is determined from the sound measured at various points in time.

* * * * *